United States Patent
Martin et al.

(10) Patent No.: US 8,464,713 B2
(45) Date of Patent: Jun. 18, 2013

(54) AUTOMATED INSPIRATORY MUSCLE TRAINING FOR PATIENTS RECEIVING MECHANICAL VENTILATION

(75) Inventors: Anatole D. Martin, Gainesville, FL (US); Michael J. Banner, Alachua, FL (US); Andrea Gabrielli, Gainesville, FL (US); Neil Russell Euliano, II, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/556,546

(22) Filed: Jul. 24, 2012

(65) Prior Publication Data

US 2012/0285456 A1 Nov. 15, 2012

Related U.S. Application Data

(62) Division of application No. 12/401,500, filed on Mar. 10, 2009, now Pat. No. 8,307,827.

(60) Provisional application No. 61/035,114, filed on Mar. 10, 2008.

(51) Int. Cl.
*A62B 7/00* (2006.01)

(52) U.S. Cl.
USPC ............. 128/204.23; 128/200.24; 128/204.21

(58) Field of Classification Search
USPC ............. 128/200.24, 204.18, 204.21, 204.23, 128/204.06
See application file for complete search history.

(56) References Cited

U.S. PATENT DOCUMENTS

| | | | |
|---|---|---|---|
| 4,838,259 A | 6/1989 | Gluck et al. | |
| 5,154,167 A | 10/1992 | Hepburn | |
| 5,303,698 A | 4/1994 | Tobia et al. | |
| 5,400,777 A | 3/1995 | Olsson et al. | |
| 5,429,123 A | 7/1995 | Shaffer et al. | |
| 5,692,497 A | 12/1997 | Schnitzer et al. | |
| 6,165,105 A | 12/2000 | Boutellier et al. | |
| 7,425,201 B2 | 9/2008 | Euliano et al. | |
| 7,461,649 B2 * | 12/2008 | Gamard et al. | 128/200.22 |
| 8,161,966 B2 | 4/2012 | Foley et al. | |

* cited by examiner

*Primary Examiner* — Glenn Richman
(74) *Attorney, Agent, or Firm* — Saliwanchik, Lloyd & Eisenschenk

(57) ABSTRACT

A system and method for automated inspiratory muscle strength exercise includes software for setting a mechanical ventilator for a pressure regulated breath with an initial pressure target that is at the highest pressure setting a patient can tolerate and increasing the pressure target as tolerated.

10 Claims, 5 Drawing Sheets

Examples of inspiratory muscle training (IMT) pressure changes

A. IMT starting at ambient (zero) baseline pressure, the change in pressure is 5 cm $H_2O$ below baseline pressure. (Spon Inh: spontaneous inhalation; Exh: exhalation)

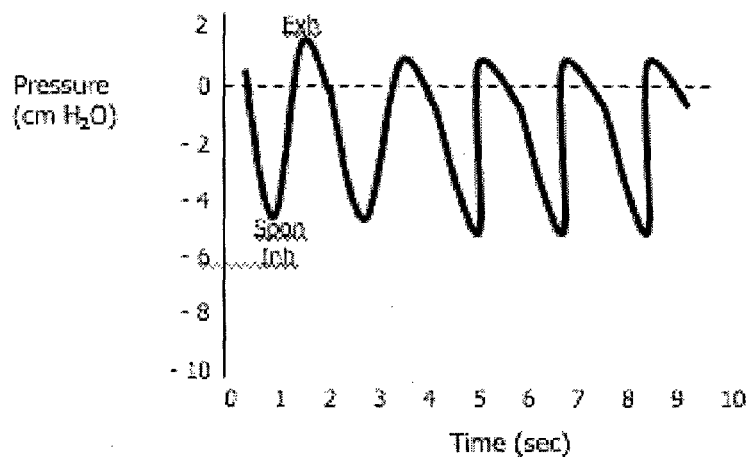

FIG. 2A

B. IMT starting at a positive end expiratory pressure (PEEP) of 5 cm $H_2O$ baseline pressure, the change in pressure is 5 cm $H_2O$ below baseline pressure. (Spon Inh: spontaneous inhalation; Exh: exhalation)

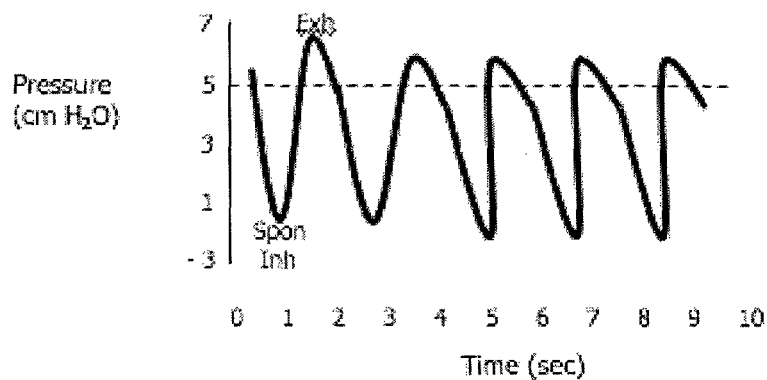

FIG. 2B

C. IMT starting at a PEEP of 10 cm $H_2O$ baseline pressure, the change in pressure is 5 cm $H_2O$ below baseline pressure. (Spon Inh: spontaneous inhalation; Exh: exhalation)

AUTOMATED INSPIRATORY MUSCLE TRAINING FOR PATIENTS RECEIVING MECHANICAL VENTILATION

CROSS REFERENCE TO A RELATED APPLICATION

This application is a divisional application of application Ser. No. 12/401,500, filed Mar. 10, 2009 now U.S. Pat. No. 8,307,827; which claims the benefit of U.S. provisional application Ser. No. 61/035,114, filed Mar. 10, 2008, herein incorporated by reference in its entirety.

GOVERNMENT SUPPORT

This invention was made with government support under a grant awarded from the National Institutes of Health under grant number NIH R01-HD42705. The government has rights in the invention.

BACKGROUND OF THE INVENTION

A patient may need ventilatory assistance as a result of disease and injuries of various kinds. The need can be direct, especially when the injury or illness afflicts the patient's respiratory system. The need can also be indirect, e.g. during anesthesia and some intensive care. The respiratory assistance can encompass everything from facilitating spontaneous breathing to total control of breathing. Mechanical ventilation (i.e., via a ventilator or respirator) is usually employed to provide the breathing assistance.

Mechanical ventilatory support is widely accepted as an effective form of therapy and means for treating patients with respiratory failure. Ventilation is the process of delivering oxygen to and removing carbon dioxide from the alveoli in the lungs. When receiving ventilatory support, the patient becomes part of a complex interactive system which is expected to provide adequate ventilation and promote gas exchange to aid in the stabilization and recovery of the patient. Clinical treatment of a ventilated patient often calls for monitoring a patient's breathing to detect an interruption or an irregularity in the breathing pattern, for triggering a ventilator to initiate assisted breathing, and for modifying or interrupting the assisted breathing periodically to wean the patient off of the assisted breathing regime, thereby restoring the patient's ability to breath independently.

Unfortunately, assistance provided by a ventilator does not precisely mimic normal ventilation. The normal mechanics of breathing are based on the active creation of a negative inspiratory pressure by the inspiratory muscles. Air is then sucked into the lungs during inhalation. Through this negative pressure in the lungs and thorax, an improved filling of the heart and increased cardiac output occur. Exhalation at rest is largely passive and follows after relaxation of the inspiratory muscles.

A problem that frequently occurs with long-term ventilator use is that the patient's inspiratory musculature becomes weakened. For example, mechanical ventilation (MV) has been shown to induce respiratory muscle dysfunction in animal models. Some studies have shown that controlled MV leads to significant losses (on the order of 25-50%) in diaphragmatic strength in as little as 12 hours in young, healthy animals. In fact, it has recently been shown that clinically significant diaphragm atrophy (~50%) occurs in humans following as little as 18-69 hours of mechanical ventilation.

In many instances following MV, the patient then loses the ability to breathe spontaneously after the problems precipitating MV support have resolved. Risks associated with ventilator dependence include increased discomfort and risk of secondary diseases for the patient (such as pneumonia, pulmonary fibrosis, aspiration, acute renal failure, cardiac arrhythmias, sepsis, vocal fold dysfunction, and barotrauma), increased morbidity and mortality, high health care costs, and longer treatment duration times. Although patients with chronic ventilator dependency (CVD) comprise only 5% to 10% of patients in intensive care units, they consume approximately 50% of all ICU resources, as measured in staff time and equipment usage. Specifically, it has been estimated that weaning patients consumed about 41% of total ventilation time in intensive care unit patients. The economic cost of long term MV dependence is enormous. Many acute care facilities charge $2,000 to $4,000 per day for long term MV support. The annual national cost of patients on a ventilator for 2 to 3 weeks, excluding physician costs, has been estimated to be $1.3 to $1.5 billion. Episodes of long term MV dependency can financially devastate families and health care institutions and are a financial drain on private insurers and government health care resources. Unfortunately, acute care MV appears to be increasing at a rate of 50% per decade.

One known way of trying to simulate normal breathing mechanics is to stimulate the respiratory muscles (in particular the diaphragm), such as by the use of electrical stimulation or magnetic stimulation of the diaphragm. However, electrical stimulation carries a risk of injury to the muscle and can be painful whereas magnetic stimulation requires an expensive magnetic stimulating device and special training for the operator.

Other methods for treating MV dependence resulting from inspiratory muscle weakness include increasing spontaneous breathing trials, pressure support breathing, T-piece breathing, weaning protocols, the administration of growth hormones, and inspiratory resistance training. All of these methods produce limited strength gains and have not been successful in weaning more than about 50% of such patients from mechanical ventilation.

For example, with inspiratory resistance training, patients undergo training by removing ventilator support and attaching an IRT device to the patient's breathing tube with variable sized orifices, usually 0.5 to 5 mm. The theory behind this method is that the when the patient breathes through increasingly smaller orifices, the pressure required to sustain inspiratory airflow will increase, thus providing a progressively increasing strength training stimulus. In practice, however, this method has a fundamental flaw: the patients can consciously vary the pressure needed to sustain inspiratory volume by altering inspiratory airflow and thus the patients control the training stimulus rather than the providers. For example, if a patient is breathing through an IRT device with a 3 mm orifice and generates an inspiratory airflow of 45 liter/min, the pressure required to sustain that airflow will be much higher compared to when the patient breathes at the same 3 mm orifice setting with an inspiratory airflow of 30 liter/min. If the patient breathes through an IRT device with an inspired airflow of 15 liters/min, the pressure (and the strength training stimulus experienced by the inspiratory muscles) will be lower than when breathing at a flow rate of 30 liter/min. Patients are able to consciously sense the amount of muscular effort needed to sustain a volitional inspiration and interpret greater inspiratory pressure requirements as a more difficult muscular effort. Since patients are able to sense the amount of muscular effort needed to sustain inspiration, when they breathe through IRT devices, they will normally adopt very low inspiratory flow rates to minimize the conscious effort of breathing, i.e., make inspiring feel easier.

While lowering the pressure required to generate inspiratory airflow by breathing with a lower flow rate will make the patient feel more comfortable, the reduced pressure requirement may be an inadequate stimulus for the inspiratory musculature to strengthen, thus lowering the effectiveness of IRT.

Despite the human and economic impact of prolonged MV dependence, there has been little research examining effective weaning treatment techniques in this population. Further, as noted above, there are no effective systems that are currently available to strengthen the inspiratory muscles and assist patients in weaning from mechanical ventilation.

BRIEF SUMMARY

In accordance with the purposes of this invention, as embodied and broadly described herein, the subject invention relates to a system and method for inspiratory muscle strength training in patients receiving mechanical ventilation support. The diaphragm is the primary muscle of inspiration and the accessory muscles of inspiration include the external intercostals, sternocleidomastoid and others. It is practically impossible to separate contributions of the various muscles of inspiration during forceful inspiratory efforts, so for the purposes of this document, inspiratory muscles refer to all of the muscles used to generate airflow into the lungs. Inspiratory muscle training, in accordance with the subject invention, aims to strengthen these muscles so that the patient can comfortably assume the task of breathing without ventilator support. The act of strength training the inspiratory muscles will not only induce the classical training effects in the inspiratory musculature (muscle fiber hypertophy, increased strength and power), but is also likely to improve the coordination of the "neural motor program" activating the numerous muscles recruited for inspiratory efforts.

One aspect of the invention relates to inspiratory muscle strength training provided by a mechanical ventilator that includes an inhalation assembly that imposes negative pressure (relative to set or baseline pressure) during inspiration so that the patient is required to generate and sustain a set number of breaths at a predetermined inspiratory training pressure for the entirety of each inspiratory act (also referred to herein as inhalation effort), thus providing a strength training stimulus to the inspiratory muscles. As defined herein, "negative pressure" and "predetermined inspiratory training pressure" are pressures that are below or less than the set pressure or baseline pressure of the ventilator. For example, if a patient's baseline or set pressure on a ventilator is 10 cm $H_2O$ end expiratory pressure (PEEP), an initial exemplary inspiratory training pressure may be 5 cm $H_2O$, 0 cm $H_2O$, or −5 cm $H_2O$ (note all of the exemplary pressure values are below the baseline pressure of 10 cm $H_2O$).

In a related embodiment, an inhalation valve assembly is provided wherein a valve restricts the flow of inspiratory gases to the patient to impose negative pressure during spontaneous patient inhalation. Once a patient is able to generate and sustain a predetermined inspiratory training pressure, the valve opens and breathing gas is provided to the patient so long as the negative pressure is maintained throughout spontaneous inhalation. Where the negative pressure is not maintained by the patient (for example, the patient is unable to generate and sustain the inspiratory training pressure), the valve either ceases to deliver flow or delivers less flow of breathing gas until the inspiratory training pressure is once again attained by the patient effort.

A method of the invention comprises providing breathing gases to a patient in such a way as to impose negative pressure on the patient, where the patient must meet or exceed a predetermined inspiratory training pressure during an entire inhalation in order to elicit breathing gases. In a related embodiment, the method further comprises the step of deriving and/or suggesting a predetermined inspiratory training pressure for a patient using a single or multiple combinations of respiratory parameters derived from a sensing assembly that monitors the patient and/or ventilator. In yet another related embodiment, the method further comprises the step of implementing in a ventilator and/or providing to a ventilator the suggested inspiratory training pressure, thus creating a closed loop system where a patient on a ventilator is placed on an inspiratory muscle training regimen automatically, without user input. Parameters for deriving an inspiratory training pressure can be derived from airway pressure, flow and volume waveforms as well as carbon dioxide and pulse oximeter waveforms normally collected by a conventional ventilator or respiratory monitor. Additional parameters include, but are not limited to, tidal volume, breathing frequency, peak inspiratory pressure (PIP), inspiratory time, $P_{0.1}$, trigger time, trigger depth, respiratory system resistance, respiratory compliance, end-tidal carbon dioxide, variations in the pulse oximeter plethysmogram, the concavity/convexity of the pressure waveform, maximal inspiratory pressure (MIP), MIP slope, MIP for the first 0.1 seconds, or other measures of inspiratory effort.

In certain embodiments, methods of the invention include using linear combination of parameters or a nonlinear combination of parameters, including but not limited to a neural network, fuzzy logic, mixture of experts, or polynomial model. Moreover, multiple different models can be used to estimate the inspiratory training pressure of different subsets of patients. These subsets can be determined by various means, including but not limited to patient condition (pathophysiology), patient physiologic parameters (lung resistance and compliance), and other parameters.

According to the invention, inspiratory muscles strength training comprises having the patient take breaths at a high intensity relative to set or baseline breathing pressure as supplied by the ventilator, where high intensity breaths typically involve 60-80% of the patient's maximal inspiratory muscle strength. One method of measuring a patient's maximal strength is by measuring the maximal inspiratory pressure the patient can develop when performing isometric contraction of inspiratory muscles. An alternative heuristic approach to gauge a patient's strength and establish a level of 60-80% of maximal patient strength is to subject the patient to an initial predetermined inspiratory training pressure that is a small step below the set or baseline pressure, preferably between 0.1 to 40 cm $H_2O$ below the set or baseline pressure, and even more preferably between 2-20 and 4-40 cm $H_2O$ below the set or baseline pressure. The patient's inspiratory performance at the predetermined inspiratory training pressure is measured by inspired tidal volume, peak inspiratory flow, and negative pressure during inspiration as well as imposed work and power of breathing generated during the loaded breaths during inspiration. Increases in inspiratory training pressure are titrated based on monitored inspiratory performance.

In one embodiment, such breaths are performed for two to five sets of six to ten inspiratory muscle strength training breaths, for a total of 12-40 training breaths per day. In a preferred embodiment, training breaths (a predetermined inspiratory training pressure was imposed on a patient during an entire inhalation act in one breath) are performed for four sets of six to ten breaths per day. By requiring increased inspiratory effort (in the form of a pressure load, resistance, or additional volume) to the patient's breathing efforts, the subject invention forces the patient to work their inspiratory muscles harder while breathing, which helps strengthen those inspiratory muscles.

According to the invention, an inspiratory muscle strength training regimen includes establishing the patient's inspiratory training pressure range from 1 to 80 cm of $H_2O$ below the set or baseline pressure, with 2 to 10,000 total breath repetitions per day. The regimen comprises establishing the patient's inspiratory training pressure at 0.5-60 cm of $H_2O$, more preferably at 1-50 cm of $H_2O$, even more preferably at 1-40 cm, more preferably at 1-30 cm of $H_2O$, and most preferably at 1-20 cm of $H_2O$ below the set or baseline pressure imposed by a ventilator on the patient. In one embodiment, an inspiratory muscle strength training regimen is initiated in a patient by having the patient breathe against an initial inspiratory training pressure at 2-4 cm of $H_2O$ pressure below baseline or set pressure with about two to ten sets of six to eight breaths a day. As the patient continues inspiratory muscle strength training in accordance with the invention, the patient's progress is monitored and imposed negative pressure is continuously adjusted in relation to the patient's progress (for example, the inspiratory training pressure is continuously adjusted) so that the patient continuously exerts 60-80% of maximal strength during inhalation. In a preferred embodiment, the patient's inspiratory muscle strength is based on monitored maximum inspiratory pressure (MIP). In certain embodiments, the number of training breath repetition sets is increased to assist in strength training as well as endurance training.

This invention, in another aspect, relates to a software and/or hardware modification to a conventional mechanical ventilator, allowing the ventilator to be used as a means of providing appropriate inspiratory muscle strength training to patients receiving mechanical ventilation support. An embodiment is directed to a control module permitting selection of adjustable inspiratory loads on the inspiratory muscles so that negative pressure is imposed on the patient during breath inhalation. For example, an inspiratory training pressure is established where the patient must meet and maintain the imposed negative pressure during the entire inhalation breath to receive any breathing gas. One possible implementation of this concept allows the user to set the ventilator in an "inspiratory muscle strength training mode," which would automatically provide inspiratory muscle strength training stimulus based on monitored patient results.

A third aspect of the invention includes an inspiratory strength training module, either incorporated into a conventional ventilator, as a stand-alone module, or as a separate module for use with conventional ventilators, which presents training breaths to the patient in accordance with the invention. Graphical feedback regarding patient progress with the training may be provided by using a display, such as an LCD screen included on most modern ventilators. In certain embodiments, real-time visual feedback is provided on a ventilator display that would allow the user to obtain immediate feedback on the effectiveness of patient training efforts.

Another aspect of the system includes an evaluation module that evaluates patient training efforts in real-time and makes recommendations to the user about modifying subsequent training efforts. For example, if the evaluation module recognizes that a patient is not working at the ideal training intensity, the module could make a recommendation to the user to increase or lower the training stimulus to optimize the training effect.

Yet another aspect of the system is a long-term trend reporting function that provides numerical and graphical data about patient progress over the duration of training. The typical patient undergoing training may require training for one to four weeks, and providing trend analysis of the training is an important component of the analysis of effectiveness. A diagnostic module can also be provided that describes the patient status (such as the current strength of the patient relative to the general population) and also status, problems or failures of the strength training regimen.

A sixth aspect of the system is a decision support function that provides clinical advice and/or closed-loop training. A decision support module can provide advice or feedback on the various attributes of the training regimen such as how often to train the patient, how many repetitions, the desired work-load, the appropriate inspiratory training pressure, and other important decisions that are required for implementing the training regimen. In addition, the system could recommend when the patient is ready for extubation, ready for weaning, or transitioning to invasive or non-invasive ventilation.

A seventh aspect is another form of inspiratory muscle training employing a closed-loop ventilator that regulates inspiratory assist pressure, for example pressure support ventilation, to control and maintain a pre-selected training/exercise load on the inspiratory muscles. The load on the muscles, measured as power of breathing (POB) or work of breathing per minute, frequency of training/exercise sessions, and duration of these sessions are physician determined. This is accomplished using special ventilator control module(s).

Accordingly, the present invention provides a method and system for assisted breathing wherein weakening of inspiratory musculature as a result of ventilator treatment is reduced or prevented. Such systems and methods also provide for assisted breathing wherein weaning time after treatment with a ventilator is shortened. In certain embodiments, inspiratory muscle strength training is automatically administered to a patient using software of the invention that is implemented on any known processor-controlled mechanical ventilator comprising either a mechanical or electromechanical valve system to control the pressure the patient must overcome to initiate a breath. Inspiratory muscle strength training strengthens or maintains inspiratory muscle function and neuromuscular efficiency during ventilation as well as assists in weaning patients from mechanical ventilator dependence. These aspects are achieved in accordance with the principles of the present invention in a method and an apparatus wherein a ventilator requires the patient to impose a negative inspiratory airway pressure with an initial pressure target that is at the highest pressure setting the patient can tolerate and increasing the negative pressure target as tolerated.

BRIEF DESCRIPTION OF THE FIGURES

FIGS. 2A-2C are graphical illustrations of training breaths initiated from various levels of positive-end expiratory pressure (PEEP)

Figure 1:
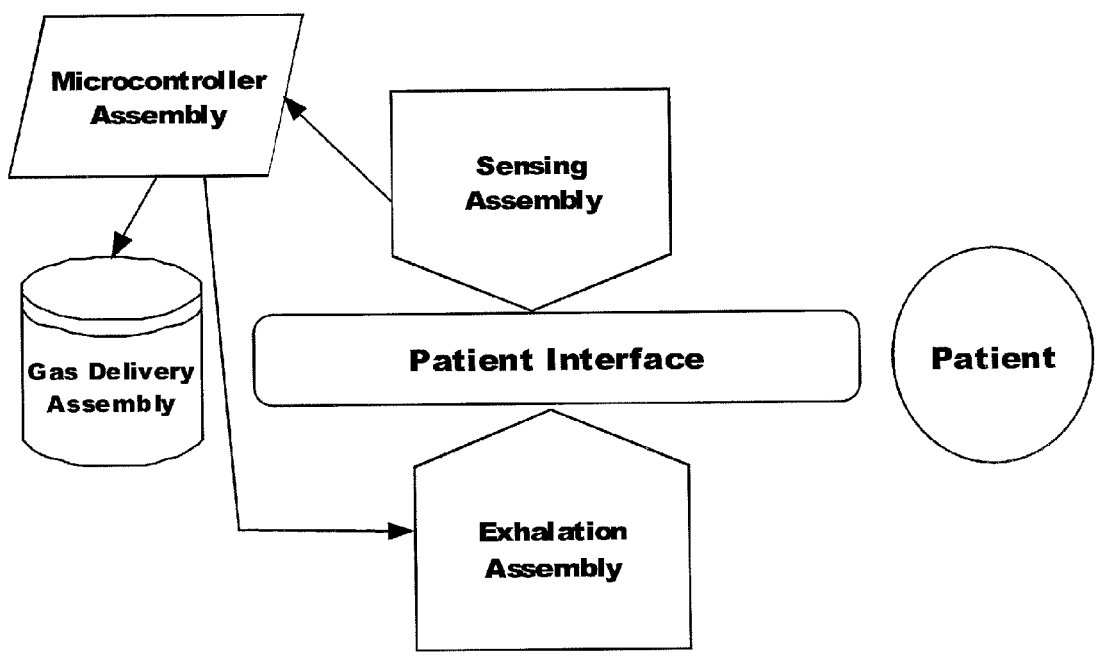
FIG. 1 is a schematic diagram showing the patient and the 5 main components of an exemplary modern electronic ventilator used in conjunction with the devices and methods of the present disclosure.

The figures may not be drawn to scale. Moreover, where directional terms (such as above, over, left, right, under, below, etc.) are used with respect to the illustrations or in the discussion, they are used for ease of comprehension only and not as limitations. The elements of the devices may be oriented otherwise, as readily appreciated by those skilled in the art.

DETAILED DISCLOSURE

In the following description, metric units and standard respiratory nomenclature as defined by the American College of Chest Physicians are employed unless otherwise stated. Particular attention is directed toward the evaluation of human subjects undergoing so-called "weaning" from mechanical ventilator dependence. Weaning is the process by which patients who have been unable to breathe without ventilator support are gradually allowed to assume a greater percentage of the muscular effort of breathing until they are able to breathe without any ventilator assistance. The system can be utilized to assist in weaning of a patient (remove from ventilator), weaning from invasive ventilation (ET-Tube or tracheostomy) to non-invasive ventilation (mask), or maintaining muscle strength throughout ventilation (invasive or non-invasive) to facilitate weaning.

The following explanation of the biomechanics of conventional weight lifting is analogous to the problems associated with weak inspiratory muscles. With weight lifting exercises, such as a biceps curl, the subject has to generate enough muscular force to overcome the gravitational force of the weight to initiate movement, and the force must be sustained throughout the entire movement of the weight to sustain movement. In prior methods for strengthening inspiratory muscles, the trigger sensitivity is set such that subjects are only required to generate a predetermined initial pressure; once this pressure setting is exceeded, no further inspiratory muscular effort is required in order for the patient to receive air from the ventilator. A weightlifting analogy of this prior methodology would be that once a subject generated enough muscle tension to move a weight a quarter of an inch, the weight would then be moved through the remaining range of motion by an external force without any further muscular effort on the part of this subject. Since generating high levels of muscle tension throughout the full range of motion is the primary physiologic stimulus that triggers muscle strength increases, the lack of a sustained muscle tension effort throughout the range of motion would be predicted to limit the strength gain.

The current disclosure describes systems and methods for inspiratory muscle strength training. In particular, the inspiratory muscle strength training system of the invention imposes a negative pressure on a patient during inhalation, wherein the patient must meet or exceed a predetermined inspiratory training pressure during the entire breath inhalation to elicit inspiratory airflow. In an alternate embodiment, the inspiratory muscle strength training system of the invention provides a pre-selected target power of breathing as an inspiratory muscle training stimulus using a closed loop ventilator. In certain embodiments, the invention includes systems and methods for gathering patient data related to performing the step above, analyzing and communicating such data to the user, and/or utilizing such data to establish appropriate inspiratory training pressure(s) and regimen (i.e., number of breaths per set, number of sets per day) for the strength training regimen.

In one embodiment, an inspiratory muscle strength training system is provided, where the system comprises a processing system and a device that supplies breathing gases to a patient. The processing system preferably provides instructions to the device, which imposes a negative pressure onto the patient during inhalation, where the patient is required to meet or exceed a predetermined inspiratory training pressure for a predetermined period of time and/or predetermined number of breaths, as established by the processing system.

An inspiratory training pressure is the amount of pressure that must be exceeded during the entirety of patient inhalation to elicit delivery of breathing gas. For example, inspiratory training pressure can be a pressure regulated breath with a pressure target that is N cm $H_2O$ below the current pressure setting or baseline pressure of the ventilator at which the patient is provided (i.e., ambient pressure plus positive end expiratory pressure (PEEP) level). It should be noted that the inspiratory training pressure of the invention is much different from setting a trigger sensitivity in a gas delivery device to N cm $H_2O$, since such a mechanism of creating a threshold pressure increases muscle workload only during the initial triggering phase and not through the entire spontaneous inhalation effort.

According to the invention, a device that supplies breathing gases to a patient can be a conventional ventilator. The conventional ventilator contemplated herein typically has a gas delivery system and may also have a gas composition control system. The gas delivery system may, for example, be a pneumatic subsystem in fluid/flow communication with a gas source of one or more breathing gases and the breathing circuit and in operative connection with the ventilator control settings of the ventilator and the processing subsystem. The breathing circuit is in fluid communication with the lungs of the patient. As one skilled in the art will appreciate, the pneumatic subsystem of the ventilator and the operative connection of that pneumatic subsystem to the source of breathing gas of the ventilator may be any design known in the art that has at least one actuator that is capable of being operatively coupled, preferably electrically coupled, to the ventilator setting controls for control of, for example, the flow rate, frequency, and/or pressure of the breathing gas delivered by the ventilator to the patient from the gas source. Such a pneumatic system is disclosed in U.S. Pat. No. 4,838,259 to Gluck et al., U.S. Pat. No. 5,303,698 to Tobia et al., U.S. Pat. No. 5,400,777 to Olsson et al., U.S. Pat. No. 5,429,123 to Shaffer et al., and U.S. Pat. No. 5,692,497 to Schnitzer et al., all of which are incorporated in their entirety by reference herein and is exemplified by the Mallinckrodt, Nelcor, Puritan-Bennet, 7200ae, and the Bird 6400 Ventilator. Although the mechanics of various ventilator designs vary, the training mechanisms described in this disclosure can be applied to all ventilator types.

According to the subject invention, a processing system is a device that includes at least one programmable digital electronic component that incorporates the functions of a central processing unit (CPU) on a single semiconducting integrated circuit (IC). The processing system can be a computer system, an embedded system, or a handheld device. The processing system is in communication with a device that supplies breathing gases, wherein commands from the processing system can control various functions of the device.

FIG. 1 illustrates an exemplary conventional electronic ventilator for use in conjunction with the present disclosure. The ventilator includes 5 main components: a gas delivery assembly, a patient interface, an exhalation assembly, a sensing assembly, and a microcontroller assembly (also referred to herein as a processing system) that monitors and/or controls the gas delivery assembly, the patient interface, the exhalation assembly, and the sensing assembly. An exemplary exhalation assembly is a gas exhaustion system that opens during patient exhalation to allow exhaled gas to leave the system. An exhalation assembly typically closes during inhalation to ensure all breathing gases reach the patient.

An exemplary patient interface includes tubing from the gas delivery assembly and the ET-Tube, mask, or other interface that delivers gas directly to the patient. This interface often includes two tubes: one for inhalation and one for exhalation. The subject invention is directed namely to the performance of the inhalation interface to ensure inspiratory muscle strength training.

An exemplary gas delivery assembly includes a regulated source of breathing gas to be delivered to the patient. The gas delivery assembly supplies breathing gas to the lungs of a patient via a breathing circuit that typically comprises an inhalation assembly and an exhalation assembly. The gas control assembly can provide pressure regulated breathing (for example with a closed loop pressure regulator) and/or flow/volume regulated breathing (for example with a proportional flow control valve (PFCV)). According to the subject invention, inspiratory muscle strength training can be administered to a patient using pressure regulated gas delivery and/or flow/volume regulated gas delivery. Moreover, inspiratory muscle strength training can be administered to a patient by manually or automatically adjusting in ventilator settings using square pressure waveforms (pressure support ventilation (PSV), bi-level positive airway pressure (BIPAP), and pressure-control ventilation (PCV)), zero change waveforms (CPAP), and more complex pressure control mechanisms (proportionally assisted ventilation (PAV)).

In a related embodiment, inspiratory muscle training using flow/volume control is based on patient monitored power of breathing (or work of breathing). Systems and methods for monitoring and estimating patient power of breathing and/or work of breathing are disclosed in U.S. Pat. No. 7,425,201, which is incorporated by reference in its entirety. With this embodiment, actual or estimated patient power of breathing (or work of breathing) is first established. For the training regimen, a target power of breathing (or work of breathing) is determined, either by the user or automatically by the ventilator (following software derived values for power of breathing/work of breathing). The target power of breathing (or work of breathing) is communicated to the ventilator to impose an inspiratory muscle training stimulus so that the patient performs a strength training regimen in accordance with the invention. Preferably, the inspiratory strength training stimulus involves adjusting ventilator settings (either manually or automatically) to manipulate the flow and/or volume of breathing gases provided to the patient so that the patient is forced to breathe at the target power of breathing. Preferably, the patient's estimated or actual power of breathing (or work of breathing) is constantly monitored and the target power of breathing (or work of breathing) is dynamically established in the ventilator for personalized inspiratory muscle training.

The sensing assembly typically consists of various sensors, including pressure and flow sensors, which gather invasive or non-invasive parameters for use in implementing the invention. The sensing assembly can be placed in the inhalation and/or exhalation patient interface. The sensing assembly can be used for control of the ventilator and in particular, the gas delivery assembly and exhalation assembly. The sensing assembly is also used to generate the standard ventilator displays.

An exemplary microcontroller assembly (or processing system) preferably includes a microprocessing subsystem that runs software for automated inspiratory muscle strength training on patients receiving mechanical ventilation. In one embodiment, the microcontroller accepts inputs from the user (such as ventilator settings) and from the sensing assembly. The microcontroller also controls the gas delivery assembly, exhalation assembly, other pneumatic components, and the user feedback via the user interface. Of particular importance, the microcontroller assembly (which can be composed of multiple controllers distributed throughout the system) is responsible for controlling the flow of breathing gas to the patient via the gas delivery assembly. The inspiratory muscle strength training system utilizes the microcontroller assembly (or processing system) to establish a negative pressure imposed onto a patient in need of inspiratory muscle strength training, where the patient must meet or exceed a predetermined inspiratory training pressure. Preferably, the microcontroller assembly controls the flow and/or volume of breathing gas to the patient so that the patient must meet or exceed the inspiratory training pressure during the entirety of patient inhalation effort in order to elicit inspiratory air flow.

A preferred embodiment of the present disclosure recognizes that in order to increase inspiratory muscle strength, the muscles should generate high tension or force levels (such as 60%-80% maximal strength or inspiratory pressure) and are generally performed for a low number of repetitions. In certain related embodiments, to increase inspiratory muscle stamina or endurance, the muscles generate moderate (such as 30%-60% maximal strength or inspiratory pressure) to high tension or force level breaths that are performed for a high number of repetitions. A typical training inspiratory muscle strength training regimen might include an intensity of 70-80% of the subject's maximal strength for two to five sets of six to ten repetitions, for a total of 12-50 repetitions per day. Thus, the preferred method is properly characterized as a strength training activity rather than as an endurance training activity.

Observational parameters related to patient response to training such as tidal volume, breathing frequency, peak inspiratory pressure (PIP), peak inspiratory flow rate, inspiratory time, $P_{0.1}$, trigger time, trigger depth, respiratory system resistance, respiratory compliance, end-tidal carbon dioxide, variations in the pulse oximeter plethysmogram, the concavity/convexity of the pressure waveform, maximal inspiratory pressure (MIP), MIP slope, MIP for the first 0.1 seconds, peak inspiratory flow, imposed power and work of breathing, or other measures of inspiratory effort/strength generated during inspiration would be used to assess intensity of patient maximal strength. For instance, patient inspired flow is monitored and where very high inspiratory flow rates and no visible evidence of fatigue are observed during inspiratory muscle strength training efforts, the training system suggests or would automatically implement increasing the inspiratory training pressure to challenge the patient inspiratory muscles more vigorously. In contrast, where the system detects (such as via the sensing assembly) very low inspiratory flow rates and tidal volumes that are abnormally low due to the patient's inability to sustain the inspiratory negative pressure, the system recommends or would automatically implement reducing the inspiratory training pressure, thus reducing the imposed negative pressure on the patient.

In an exemplary embodiment of the present disclosure, a waveform selected for implementing an inspiratory training pressure would be similar to a negative N cm $H_2O$ CPAP or PSV breath, where no flow would be delivered until the trigger pressure reached N cm $H_2O$ below baseline, and then the gas delivery assembly would be controlled to deliver just enough gas to the patient to maintain the pressure at N cm $H_2O$ below baseline. After triggering, the flow waveforms would be similar to a normal breath, except that the negative pressure regulated breath would require significantly greater effort to achieve.

Figure 2C:
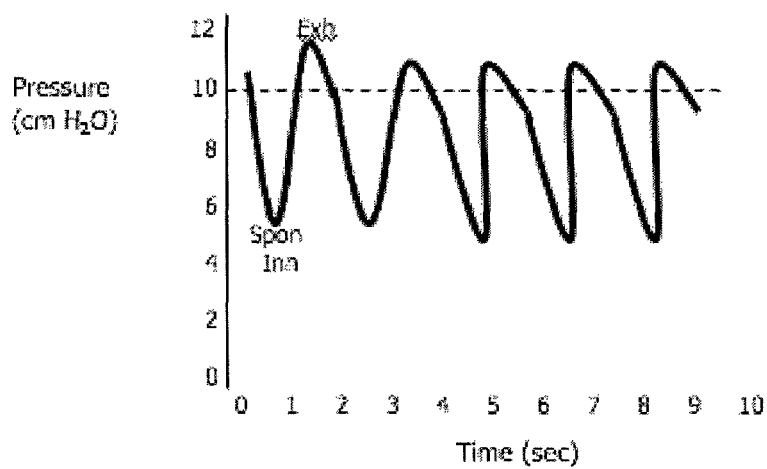

FIG. 2A-2C show training breaths initiated from various levels of positive-end expiratory pressure (PEEP). FIG. 2A shows inspiratory muscle training (IMT) breaths initiated at an ambient baseline pressure (zero pressure), following which negative pressure was imposed on the patient such that the training breaths were performed at an inspiratory training pressure of 5 cm $H_2O$ below the baseline pressure. Note that the inspiratory training pressure was set at $-5$ cm $H_2O$. FIG. 2B shows inspiratory muscle training (IMT) breaths initiated at a positive baseline pressure (PEEP) of 5 cm $H_2O$, following which negative pressure was imposed on the patient such that the training breaths were performed at an inspiratory training pressure of 5 cm $H_2O$ below the baseline pressure. Note that the inspiratory training pressure was set at 0 cm $H_2O$. FIG. 2C shows inspiratory muscle training (IMT) breaths initiated at a positive baseline pressure (PEEP) of 10 cm $H_2O$, following which negative pressure was imposed on the patient such that the training breaths were performed at an inspiratory training pressure of 5 cm $H_2O$ below the baseline pressure. Note that the inspiratory training pressure was set at 5 cm $H_2O$.

Because the training breath is similar to a standard pressure regulated breath, the inspiratory strength training mode could be implemented automatically in microprocessor controlled ventilators by only modifying the ventilator control and user interface software, thus providing a simple upgrade or product improvement.

The above description assumes a standard electronic ventilator and is used for example only. Other mechanisms for imposing negative pressure are also possible. For example, on pneumatic ventilators, PEEP valves can be used in a reverse direction so that they do not open until the predetermined inspiratory training pressure setting is reached. Once the training pressure is reached and maintained, breathing gas is supplied to the patient. Should the patient fail to maintain the training pressure, the valve is closed to prevent supply of breathing gas to the patient. On electronic ventilators, these same PEEP valves can be electronically switched into the circuit during the prescribed training times via the use of electro-pneumatic on-off or three-way valves.

An exemplary training regimen involves four sets of approximately 10 training breaths per day with a recovery period between each set of training breaths. The training breaths are performed during a single episode and usually require approximately 15 minutes from initiation to completion of a training round. The adjustable parameters of the training regimen include the number of breaths during each set, the number of sets per day, and the desired inspiratory training pressure. These parameters are set heuristically in an exemplary method. For example, the inspiratory training pressure is set initially to a low value (about 4-6 cm $H_2O$) and increased daily as the patient's inspiratory muscles become stronger.

A wide variety of possible feedback mechanisms may be used instead of a heuristic parameter adaptation with the subject invention. For example, an inspiratory muscle strength training regimen can be manipulated via work of breathing (WOB) feedback in a ventilator. Total work of breathing is the amount of work necessary to initiate and sustain a breath. During spontaneous or assisted ventilation, total work of breathing is the work exerted by the patient to obtain gas exchange from the ventilator for a breath. The total work of breathing can be measured and quantified in Joules/L of ventilation. All methods for deriving work of breathing, including observation, derivation of work of breathing through invasive and non-invasive observational data, as well as derivation of estimated work of breathing through invasive and non-invasive observational data, are contemplated for use herein in establishing inspiratory muscle strength training regimens.

According to certain embodiments of the invention, inspiratory muscle strength training is applied to closed-loop control of mechanical ventilation. Closed-loop mechanical ventilation, sometimes known as "complete automatic control" of mechanical ventilation describes a variety of well-known techniques in ventilation. In the simplest form, closed-loop ventilation is the control of one output variable of the mechanical ventilator based on the measurement of an input variable. For example, pressure support ventilation (PSV) uses closed-loop control where clinician sets a target pressure (the pressure support setting) and flow is automatically adjusted to maintain that pressure throughout inspiration. As the ventilator monitors airway pressure (the target), the control algorithm continuously modulates the flow (the output) to achieve the desired pressure. More complex forms of closed-loop ventilation involve measurement of multiple inputs (i.e., compliance, oxygen saturation, respiratory rate) to control multiple outputs (i.e., ventilator frequency, airway pressure, tidal volume). The latter type of control more closely mimics the ventilatory control and response of human physiology.

In one embodiment of the invention, inspiratory muscle strength training is adapted in a closed-loop mechanical ventilator that regulates inspiratory assist pressure in order to control and maintain a training/exercise load on the inspiratory muscles. Load on the inspiratory muscles is also referred to herein as "power of breathing", which is the rate of total work that is performed; for example, power of breathing can be quantified as work of breathing per minute. According to the subject invention, the user can either prescribe a training/exercise load on the inspiratory muscles or the user can have the ventilator derive an appropriate regimen based on multiple parameters (i.e., maximal inspiratory pressure ($P_{-1}$), trigger pressure slope, pressure time product (PTP), flow volume or pressure volume loops, pulse-plethysmographic data) and implement the training/exercise load on the inspiratory muscles.

In a related embodiment, pressure support ventilation (PSV), or a similar mode of ventilatory support providing inspiratory assist pressure, is automatically up- and down-regulated by a closed-loop ventilator to maintain power of breathing in a normal range for example to treat a patient. When the patient is to undergo inspiratory muscle strength training in accordance with the invention, power of breathing is temporarily maintained at a higher range than that of normal range. This is accomplished by having the closed-loop ventilator down-regulate the inspiratory assist pressure, causing power of breathing to increase to a higher range. Once established at this higher range, the closed-loop ventilator automatically regulates inspiratory assist pressure to maintain the increased power of breathing. When the exercise/training session is completed, the closed-loop ventilator automatically increases inspiratory assist pressure to restore power of breathing to back down to normal treatment levels.

Figure 4:
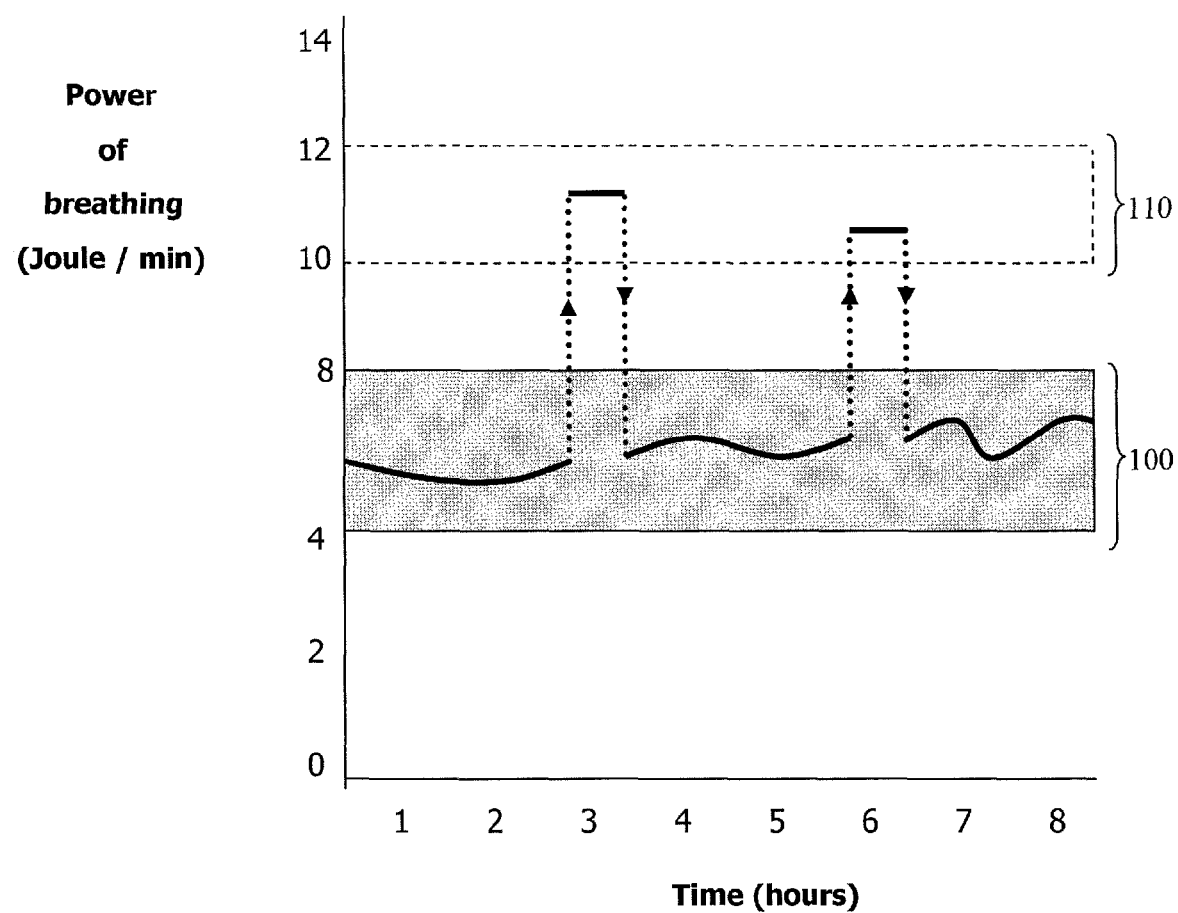
FIG. 4 is a graph showing a ventilator trend display over eight hours with a patient under normal breathing conditions and a patient subjected to inspiratory muscle strength training using a target power of breathing or work of breathing per minute.

FIG. 4 illustrates this embodiment, where a ventilator trend display is provided over eight hours with a patient under normal breathing conditions and a patient subjected to inspiratory muscle strength training. 100 denotes normal or assisted power of breathing range as provided by a ventilator. 110 denotes a preselected inspiratory muscle training range of 10 to 12 Joules minute. The patient exercises/trains in this range 110 every three hours, for 15 minutes per session. The load on the inspiratory muscles (power of breathing exercise), frequency, and duration of the exercise/training sessions can be physician-derived or provided by the ventilator, as described herein. In certain embodiments, the ventilator can automatically derive appropriate load on inspiratory muscles and/or automatically administer the appropriate load on inspiratory muscles. In related embodiments, a selection regarding various inspiratory muscle loads is provided by the ventilator and can be selected by the user and/or automatically selected by the ventilator following derivation of appropriate power of breathing exercise.

Other feedback mechanisms for use with the subject invention include flow-independent or flow-constant parameters; pressure-independent or pressure-constant parameters; intra-training, inter-training, muscle strength parameters or response parameters that indicate physical stress (such as blood pressure, heart rate, electrocardiogram (ECG), for example); maximum inspiratory pressure (MIP) and derivatives, the volume of $CO_2$ exhaled ($VCO_2$) or the volume of oxygen taken into the lungs ($VO_2$); isometric or isotonic measures (e.g. parameters that measure the airway changes before and after the inspiratory training pressure is reached); parameters derived by ventilator interactions with the patients (e.g. measurements of peak inspiratory flow (PIF) resistance, or $P_{.01}$ during a temporary occlusion of the breathing circuit during a breath); standard breath-based analysis such as tidal volume, flow rates, inspired:exhaled (I:E) ratio; and non-training breath analysis, for example recognizing that stronger patients will respond better to normal breathing as well as breathing during training.

In certain embodiments, the inspiratory muscle strength training system is able to address emergent situations. For example, where the patient is struggling or unable to properly perform in accordance with inspiratory muscle strength training protocols, the system includes failsafe measures to ensure that proper, safe gas delivery is provided to the patient at all times. It is noted that the patient's health and safety are of greater importance than ensuring full compliance with IMST protocols.

Inspiratory muscle strength training is typically a multi-day or multi-week rehabilitation task that must be monitored for optimal results. As such, an exemplary embodiment of a training system of the current disclosure include means for producing detailed trending information of the various parameters of interest before, after, and during the training rounds. These parameters could include all or some of the parameters listed above, as well as performance parameters and safety features. Trending plots could be displayed on the ventilator to show the patient response to training and improvements. Readiness for weaning could be determined and displayed as well. Readiness for muscle training could also be determined by monitoring patient characteristics.

In certain embodiments, a training bout can be initiated by the support staff (nurse or respiratory therapist, for example) or by the ventilator itself. If the regimen is programmed into the ventilator, the ventilator could provide an audible or electronic notification to the support staff to assist with the training. In particular, intra- and interday training parameters can be displayed during training and used as goals or targets to provide patient feedback that can dramatically improve results. In particular, many patients on ventilators feel helpless and unable to breath without the ventilator. Obtaining training feedback provides tremendous motivation to the patients to actively participate in the muscle training Patient or support staff feedback can be provided on the existing ventilator display or on a special remote or wireless display system. A wireless display system may be similar to a personal digital assistant (PDA), laptop personal computer (PC), iPOD, or other commercial display system that can be easily programmed to communicate with the ventilator.

In one embodiment of the invention, the method for inspiratory muscle strength training comprises use of a mathematical model, such as a neural network, wherein the neural network imposes negative pressures for the patient based upon input data (provided either by the user or derived from a ventilator or respiratory monitor), wherein the input data includes at least one of the following parameters: work of breathing, power of breathing, the airway pressure, flow, airway volume, carbon dioxide flow, and pulse oximeter plethysmogram waveforms normally collected by a respiratory monitor, including but not limited to tidal volume, breathing frequency, peak inspiratory pressure (PIP), inspiratory time, $P_{.01}$, trigger time, trigger depth, respiratory system resistance, respiratory compliance, end-tidal carbon dioxide, variations in the pulse oximeter plethysmogram, and the concavity/convexity of the pressure waveform, wherein the inspiratory training pressure is provided as an output variable.

In the above-noted method, the model is trained by clinical testing of a test population of patients to obtain teaching data, the teaching data which includes the above-noted input information. The teaching data is provided to the model, whereby the model is trained to provide an output variable corresponding to the inspiratory training pressure.

The invention contemplates an inspiratory muscle strength training system that comprises a model which first receives as input primary teaching data obtained from clinical testing of a test population of patients, whereby the model learns the teaching data and is trained to provide an output variable for an inspiratory training pressure, such that when the model receives patient input data in the form of the above-noted parameters obtained from a patient, the model provides the output variable for estimating the inspiratory training pressure for that patient.

Aspects of the invention, namely protocols for inspiratory muscle strength training, may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In one embodiment, the present invention takes the form of a computer-program product that includes computer-useable instructions for inspiratory muscle strength training, embodied on one or more computer-readable media.

As a computer readable media containing program instructions, an embodiment of the invention includes: computer readable code devices for receiving input variables, processing the input, and providing an output indicative of inspiratory training pressure. In a preferred embodiment, processing comprises utilizing a neural network. The method may further include controlling a ventilator in response to the output (inspiratory training pressure) obtained.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

Inspiratory Strength Training Device

In addition to the above description, it is possible to build an inspiratory muscle strength training system to be used either alone or in conjunction with existing ventilators, where the strength training system implements the training regimen similar to that described above.

In one embodiment, an inspiratory muscle strength training system comprises a gas delivery system operably connected to PEEP valves controlled by a processing system. In one embodiment, the system is an independent device where the patient would periodically be removed from the ventilator and breathe through the independent automatic training device and then placed back on the ventilator after training. In another embodiment, the system is removably implemented as an upgrade to an existing ventilator through an auxiliary connection to the patient circuit or other methodology for integrating the device with the ventilator. In the preferred embodiment, both the independent training device and the ventilator upgrade system would include a display with patient feedback, historical data, and other pertinent information.

Following is an example that illustrates procedures for practicing the invention. This example should not be construed as limiting.

EXAMPLE 1

A single blind, randomized trial of inspiratory muscle strength training (IMST) in failure to wean (FTW) patients was conducted. Assigned groups of patients were similar with respect to age, gender, cause of respiratory failure, smoking history, SAPSII score (a mortality prediction index, where higher values suggest a high death probability), MV settings, arterial blood gases when receiving full MV support, $P_aO_2/F_iO_2$, prealbumin, duration of spontaneous breathing trials (SBT) tolerated (IMST 2.4±7.3 hours, p=0.84) and maximal volitional negative inspiratory pressure. Patients did not know if they had been assigned to the IMST or sham (control) training group.

Figure 3:
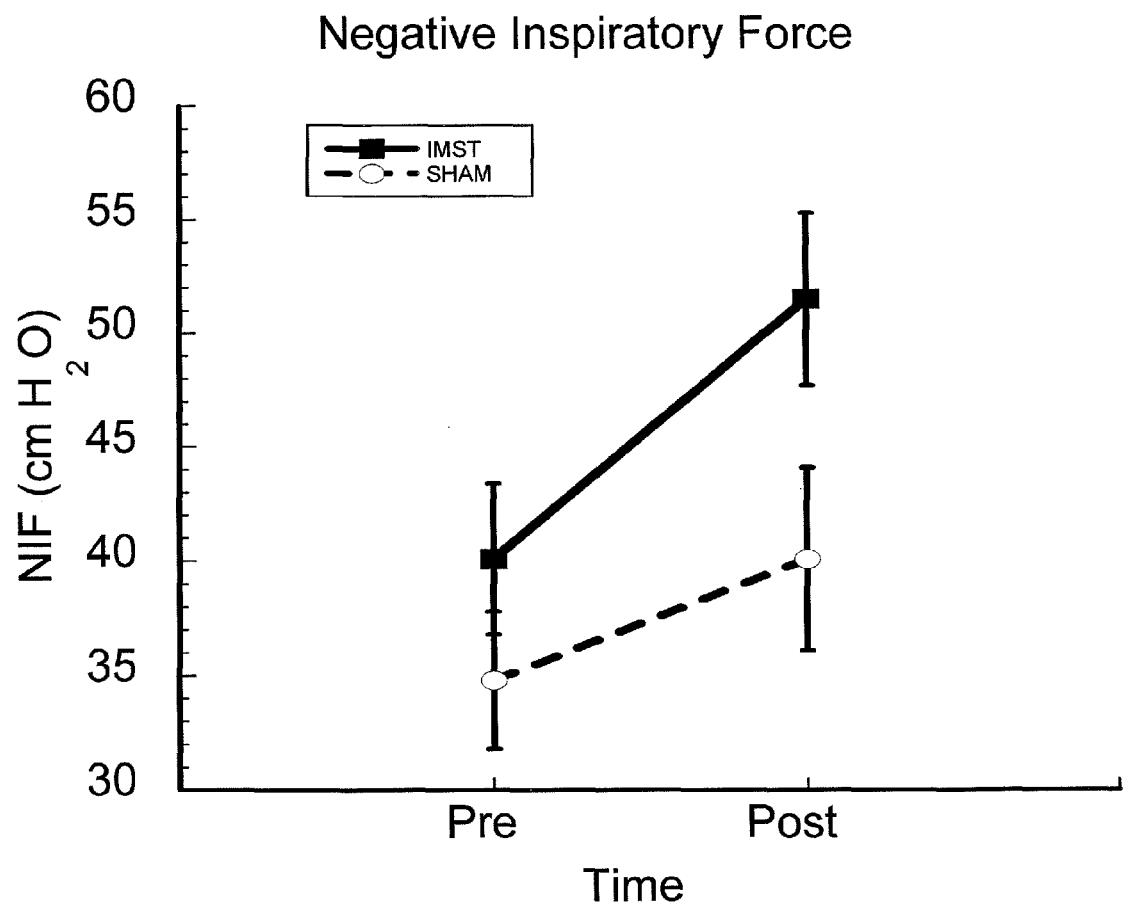
FIG. 3 is a graph showing that repeated measures ANOVA for negative inspiratory force (NIF) revealed significant effects for treatment and time.

IMST consisted of 4 sets of 6-10 breaths through a threshold inspiratory (Respironics Threshold PEP) device attached to a tracheotomy tube at the highest pressure setting the patients could tolerate. The initial training pressure setting was determined by starting at 4 cm $H_2O$ and increasing until the patient was unable to open the valve. The pressure was increased daily as tolerated. IMST training was conducted 5 days/week. All patients also participated in progressively lengthening spontaneous (no MV support) breathing trials 7 days/week on the following schedule: 1 hour, 2, 3, 4, 6, 9, 12 and off as tolerated. SBTs were ended if patients exhibited a 30 beat or more increase in heart rate, systolic blood pressure >180 mm Hg or <90, $S_pO_2$ dropped to <90% for 5 minutes, respiratory rate >35 for 5 minutes, serious dysarrhythmias, the patient requested to be returned to MV support, or showed clinical evidence of respiratory distress. Subjects were treated for up to 28 days. Patients were considered weaned when they could tolerate 72 consecutive hours of spontaneous breathing without MV support. The IMST group had received 41±2 days of MV support before starting intervention. 16 of 21 (76%) patients assigned to the IMST treatment were weaned, p=0.01. The IMST group's pressure setting on the training device increased from −5.5±1.1 to −12.7±3.6 cm $H_2O$ from pre to post-training, p<0.0001. The negative pressure imposed by the IMST device during the training breaths increased from −9.5±4.0 to −15.2±6.3 cm $H_2O$ from pre to post training, p<0.001. FIG. 3 is a graph showing that repeated measures ANOVA for maximal negative inspiratory force (NIF) revealed significant effects for treatment and time. The interaction effect was not significant, p=0.13, data are mean±SEE).

COMPARATIVE EXAMPLE 1

"SHAM" training in FTW patients was conducted as a control. Assigned groups of patients were similar with respect to age, gender, cause of respiratory failure, smoking history, SAPSII score (a mortality prediction index, where higher values suggest a high death probability), MV settings, arterial blood gases when receiving full MV support, $PaO_2FiO_2$, prealbumin, duration of spontaneous breathing trials (SBT) tolerated (SHAM 2.2±3.5, p=0.84) and maximal volitional negative inspiratory pressure. The SHAM treatment consisted of inspiring through a modified resistive inspiratory muscle training device (Respironics Pflex) that provided minimal strength training stimulus (<−4 cm $H_2O$ at a flow rate of 30 l/min resistive pressure loads during tidal breathing). SHAM training was conducted 5 days/week. All patients also participated in progressively lengthening spontaneous (no MV support) breathing trials (SBT) 7 days/week. Subjects were treated for up to 28 days. The weaning criterion was 72 consecutive hours of spontaneous breathing without MV support. The SHAM group received 50±40 ($p=0.39$) days of MV support before starting intervention. 6 of 17 (35%) SHAM subjects were weaned, $p=0.01$, compared to the training group.

Of the subjects weaned, the IMST group required 13.3±7.5 days of treatment, while the SHAM group required 18.5±8.4 days ($p=0.04$, 1 tailed T test). The results of Example 1 and Comparative Example 1 show that IMST plus SBT led to an improved weaning outcome when compared to SHAM plus SBT in that more FTW subjects were weaned and weaned sooner.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. One or more computer-readable media having computer-useable instructions embodied thereon for performing a method of inspiratory muscle strength training, the method comprising:
   providing a sensing assembly and gas delivery device having an inhalation assembly that provides inspiratory air flow to a patient;
   imposing delivery of inspiratory air flow using an inspiratory training stimulus; and
   controlling the inhalation assembly to deliver inspiratory air flow using the inspiratory training stimulus during an entire inhalation act for every breath by the patient.

2. The media of claim 1, wherein the gas delivery device is a mechanical ventilator.

3. The media of claim 1, wherein the inspiratory training stimulus is a pressure between 1 to 80 cm of $H_2O$.

4. The media of claim 3, wherein the inspiratory training pressure is between 2-20 cm of $H_2O$.

5. One or more computer-readable media having computer-useable instructions embodied thereon for performing a method of inspiratory muscle strength training, the method comprising:
   receiving respiratory parameters of a patient from a sensing assembly;
   calculating an inspiratory training stimulus variable from the respiratory parameters; and
   providing said inspiratory training stimulus variable to a gas delivery device, wherein said gas delivery device delivers inspiratory air flow to the patient and comprises settings for adjusting the inspiratory airflow; and
   adjusting the gas delivery settings to administer air flow to the patient to impose negative pressure on the patient during inhalation at the inspiratory training stimulus variable.

6. The media of claim 5, wherein the gas delivery device is a mechanical ventilator.

7. The media of claim 5, wherein the inspiratory training stimulus is a pressure between 1 to 80 cm of $H_2O$.

8. The media of claim 7, wherein the inspiratory training pressure is between 2-20 cm of $H_2O$.

9. The media of claim 5, wherein the inspiratory training stimulus is a target power of breathing.

10. The media of claim 5, wherein the method further comprises:
   receiving a second set of respiratory parameters of the patient comprising a response of the patient to the inspiratory training stimulus;
   calculating a second inspiratory training stimulus variable from the second set of respiratory parameters;
   providing said second inspiratory training stimulus variable to the gas delivery device;
   adjusting the gas delivery settings to administer air flow to the patient to impose negative pressure on the patient during inhalation at the second inspiratory training stimulus variable; and
   repeating the steps herein as necessary.

* * * * *